United States Patent [19]

Gelbein

[11] 4,262,138

[45] Apr. 14, 1981

[54] PREPARATION OF CARBOXYLIC ACID ESTERS WITH BF$_3$ COMPLEX CATALYST

[75] Inventor: Abraham P. Gelbein, Plainfield, N.J.

[73] Assignee: Chem Systems Inc., New York, N.Y.

[21] Appl. No.: 28,459

[22] Filed: Apr. 9, 1979

[51] Int. Cl.$^3$ .............................................. C07C 67/38
[52] U.S. Cl. ................................... 560/233; 203/63;
203/66; 560/214; 560/248
[58] Field of Search .............................. 560/233, 248;
260/410.9 R; 203/63, 66

[56] References Cited

U.S. PATENT DOCUMENTS

| | | | |
|---|---|---|---|
| 2,378,009 | 6/1945 | Hanford et al. | 560/233 |
| 2,967,873 | 1/1961 | Koch et al. | 560/233 |
| 3,349,107 | 10/1967 | Pawlenko | 560/233 |

OTHER PUBLICATIONS

Pawlenko, Chemie. Ing. Techn., 40, 52 (1968).
Moller, Bernstoff–Chemie., 45, 129 (1964).

*Primary Examiner*—Vivian Garner
*Attorney, Agent, or Firm*—Bert J. Lewen

[57] ABSTRACT

In a process wherein ethylene or propylene is carbonylated with carbon monoxide to form carboxylic acid esters in the presence of a catalyst complex of one mole of BF$_3$ and one mole of alcohol, the invention concerns a technique wherein the catalyst is recovered from the reaction product and recycled. The carbonylation is carried out until approximately one-half of the alcohol is consumed, to form a reaction mass containing the BF$_3$, the alcohol, and the carboxylic acid ester in a 2:1:1 molar ratio. In the first step, the one mole of the free BF$_3$ is vaporized from the reaction mass. The remaining admixture is a 1:1:1 mixture of the three aforesaid compounds. To this mixture additional alcohol is added and the mixture is subjected to distillation. A carboxylic acid ester/alcohol azeotrope and residual alcohol are removed by the distillation, to leave a residue containing a 1:2 BF$_3$/alcohol complex. This complex is combined with an additional mole of BF$_3$ to form the 1:1 catalyst complex used in the carbonylation. The additional mole of BF$_3$ is preferably that initially separated from the reaction mass; however, it may be obtained from an external source. The carboxylic acid ester/alcohol mixture may be separated by azeotropic distillation using an azeotroping agent, such as octane, to recover the alcohol-octane as overhead product and the carboxylic acid ester as bottoms product.

7 Claims, No Drawings

PREPARATION OF CARBOXYLIC ACID ESTERS WITH BF₃ COMPLEX CATALYST

BACKGROUND OF THE INVENTION

It has long been desired to find an inexpensive means of making alkyl methacrylate and alkyl acrylates, basic monomers for the formation of acrylic resins, as well as acrylic and methacrylic acids. Conventionally, methyl methacrylate is prepared by reacting acetone and hydrogen cyanide to form cyanohydrin; dehydrating the cyanohydrin in the presence of sulphuric acid to form methacrylamide sulfate; and finally reacting the sulfate with methanol and sulphuric acid to form the desired methyl methacrylate. Because of the high cost of the raw materials and the need to dispose of by-product ammonium sulfate, this process is deficient.

Other proposed processes for making methyl methacrylate and methacrylic acid involve isobutylene oxidation, ammoxidation, epoxide formation and t-butanol oxidation. These processes also suffer from high capital costs and, in some cases, raw material costs.

In assignee's co-pending application Ser. No. 28,460 filed this even date entitled "BF₃ Complex Catalyst for Preparing Acids and Esters," a process is described for making carboxylic acid esters, e.g., alkyl methacrylates and alkyl acrylates, by the carbonylation of ethylene or propylene with carbon monoxide in the presence of a catalyst complex composed of one mole of methanol and the olefin propylene, the product is methyl isobutyrate. This latter compound may be dehydrogenated to prepare methyl methacrylate. This process is advantageous because the end products are formed from raw materials, no by-products are formed, and the capital costs are economically attractive.

The process described in the aforesaid co-pending application, while extremely attractive for the foregoing reasons, suffers from the drawback that catalyst complex could not be easily recovered for reuse. As a matter of fact, in discussing this specific catalyst for use with cyclic olefins, Moller in Brennstoff-Chemie 45, 129 (1964), said that the catalyst BF₃.CH₃OH would be of little interest because it cannot be recovered in usable form. This is because there is no known way to separate the reacting ester product from the complex without destroying the BF₃, e.g., by hydrolyzing it with water to form fluoroboric acids.

BRIEF SUMMARY OF THE INVENTION

This invention relates to a process for preparing low molecular weight saturated carboxylic acid esters from ethylene and propylene by carbonylation with carbon monoxide and a complex catalyst composed of one mole of BF₃ and one mole of an alcohol. More specifically, the invention relates to the recovery and recycle of the catalyst in a convenient and economical manner.

In the process of the invention, the olefin is carbonylated with carbon monoxide in the liquid catalyst complex until substantially one-half of the alcohol is consumed. This results in the formation of a reaction mass consisting of the carboxylic acid ester, the alcohol, and the BF₃ in a molar ratio of 1:1:2 which is then subjected to a distillation step wherein one-half of the BF₃ is removed as a distillate fraction. The bottoms product from this step consists of the same components in a molar ratio of 1:1:1. This mixture is then further distilled after sufficient additional alcohol is added to form a low boiling azeotrope with all of the carboxylic acid ester. This azeotrope is recovered as an overhead product. The residue material remaining is a BF₃/alcohol 1:2 complex. This material may be easily reconstituted to form the 1:1 complex catalyst by the addition of free BF₃, the latter of which may be that initially separated from the reaction mass. The carboxylic acid ester and alcohol stream is combined with an azeotroping solvent and said combination is subjected to further distillation wherein a low boiling azeotrope comprised of solvent and alcohol is removed from the carboxylic acid ester.

DETAILED DESCRIPTION OF THE INVENTION

In the present invention, gaseous feedstocks consisting of either propylene or ethylene and carbon monoxide are used. The olefins may be obtained from any source, most generally from steam cracking of hydrocarbons.

The carbon monoxide employed should have a purity of at least 99%, though mixtures of carbon monoxide and other inert gases, such as carbon dioxide, may be used.

It is preferred that the olefin and carbon monoxide be of high purity since this will simplify product recovery and minimize losses in purge streams required to remove inerts from the reaction system.

The reaction may be carried out at temperatures of from 0° C. to 100° C., preferably from 20° C. to 60° C. The temperatures should be kept at moderate levels throughout the process because high temperatures could result in the formation of by-products, especially heavier esters.

In the carbonylation reaction of the invention, one mole of carbon monoxide reacts with each mole of olefin. This is known as the external reactant ratio. On the other hand, it is desirable to maintain a large molar excess of carbon monoxide in the vapor phase in order to suppress undesirable side reactions. This ratio (known as the internal carbon monoxide to olefin molar ratio) is controlled by the system pressure, degree of agitation, and purge rate and is broadly at least 5:1, preferably at least 8:1. As a practical matter, ratios of not more than 1000:1, preferably not more than 100:1, are used.

In view of the foregoing, it will be understood that in a batchwise process and during the start-up of a continuous process a large molar excess of the carbon monoxide is fed. However, in the continuous process, once steady state conditions are achieved, only about one mole of carbon monoxide is fed to the reactor for each mole of olefin.

The reaction pressure, while not critical, is generally from 10 to 300 atmospheres, most preferably from 30 to 100. While higher pressures are not detrimental and in some instances actually favor selectivity to the desired products, again practical considerations such as equipment design and safety factors favor the use of the pressure ranges set forth above.

The catalyst complex used in the instant invention contains equal molar amounts of boron trifluoride and alcohol. These catalysts are stable complexes having specific physical properties. They exist as liquids at room temperature and therefore can be conveniently used as the reaction solvent.

While it is understood that the 1:1 molar ratio catalyst is the active constituent, the catalyst may be prepared using ratios of from about 0.75 to 10 moles of boron trifluoride for each mole of the alcohol, preferably from 0.75 to 2 moles per mole. It will be understood that, when less than one mole of the boron trifluoride is utilized with, say, methanol, the catalyst is a mixture of $BF_3.CH_3OH$ and $BF_3.2CH_3OH$. This latter compound is also a stable complex; however, in contrast to the 1:1 molar ratio catalyst, it is non-selective to the desired product and of relatively low activity. Accordingly, a substantial amount of such complex is undesirable.

On the other hand, where the molar ratio is in excess of 1:1, the 1:1 catalyst complex (e.g., $BF_3.CH_3OH$) is in admixture with uncomplexed boron trifluoride. Since the boron trifluoride is not catalytically active, sizeable excesses are of little advantage.

As noted above, in performing the process of the invention it is advantageous to use the catalyst as the reaction medium. Other organic constituents may be present, so long as they do not interfere with the carbonylation. The reaction period is not critical, but should be selected so as to achieve acceptable conversions without unduly lengthening the process cycle. As a practical matter, the reaction period ranges from about 10 minutes to 3 hours.

To form the $BF_3$ catalyst complex, it is most desirable to use methanol as the alcohol. In addition, it has been found that other catalyst additives such as hydrogen fluoride, sulphuric acid, phosphoric acid, are not necessary for the synthesis of the desired products.

To produce methyl isobutyrate, the carbonylation is continued until one-half of the methanol is consumed in the formation of the methyl isobutyrate product. The resulting product mixture has a composition consisting of methyl isobutyrate, methanol and $BF_3$ in a molar ratio of 1:1:2.

This reaction mass is stripped in a countercurrent contacting tower to separate half the $BF_3$ contained therein as a vapor overhead product and to produce a residue product containing equimolar amounts of methyl isobutyrate, methanol and $BF_3$ (hereinafter the "1:1:1 complex"). Operating conditions for this step depend on the vapor-liquid equilibria for the system and can be varied over a wide range of temperatures and pressures. The separation is conveniently done at ambient pressure and at approximately 85° C., the boiling point of the 1:1:1 complex. Under these conditions, the stripping action is provided by the boiling 1:1:1 complex vapors which are generated in the bottom of the stripping column. These vapors flow countercurrently to the reaction mixture feed which is fed at the top of the column. Alternatively, the column can be operated at a temperature and pressure wherein the 1:1:1 complex does not boil by using an inert stripping gas, e.g., nitrogen, introduced at the bottom of the column. Generally, it is preferred to maintain the column temperature below 100° C. to minimize by-product formation.

After the separation of the $BF_3$, the residue contained equimolar quantities of $BF_3$, methanol and the methyl isobutyrate. The methyl isobutyrate and the $BF_3$ contained in this residue from the stripping step cannot readily be recovered by means known to the art without destroying the catalyst complex. For example, $BF_3$ or the organic components cannot be preferentially stripped from this complex, nor are there any known extraction techniques which will preferentially extract the $BF_3$ or the organic components. Methods known to the art for making the separation involve reaction of the $BF_3$ with another component, e.g., water or sodium chloride. In the first case hydrolysis of the $BF_3$ occurs with release of the organic components. In the second case a $BF_3$/sodium chloride compound is formed with release of the organic components. However, there is no known practical method for recovering the $BF_3$ from the $BF_3$ hydrolysis compounds or the $BF_3$/sodium chloride compound.

In accordance with the invention, to separate the desired components, methanol is added to the 1:1:1 complex, preferably in a distillation zone. The amount of methanol added corresponds to at least that required to produce a methyl isobutyrate/methanol azeotrope as an overhead product and a bottoms product consisting of a complex of $BF_3/CH_3OH$ in 1:2 molar ratio. The composition of this azeotrope, at an atmospheric pressure, is 75 weight percent methanol, 25 weight percent methyl isobutyrate. This is equivalent to a methanol/methyl isobutyrate molar ratio of 9.56. Thus, if the distillation is conducted at ambient pressure at least 10.56 additional moles of methanol must be added to the distillation zone. Technically there is no upper limit to the amount of methanol that can be added. The amount that is added is dictated by the design of the distillation equipment wherein energy requirements are balanced against equipment costs.

The separation is conveniently carried out in a conventional continuous distillation column containing trays or packing. The 1:1:1 complex is generally fed near the middle of the column with the methanol added above this feed point. The distillate fraction from this column is a low boiling methanol/methyl isobutyrate azeotrope and any additional uncomplexed methanol. The bottoms product is a $BF_3$/methanol complex in 1:2 molar ratio. Operating temperatures and pressures for the column are a function of the vapor pressure-temperature curve for the complex since this is the material boiling in the reboiler. Typical pressure-temperature data is given below:

| Temperature, °C. | Vapor Pressure, mm Hp |
|---|---|
| 57 | 4 |
| 130 | 100 |
| 200 | 760 |

Preferred operating temperatures are from 50° to 200° C. These temperatures minimize side reactions which can lead to yield losses and complicate subsequent purification steps.

The $BF_3$/methanol 1:2 bottoms product from the column is combined preferably with the $BF_3$ originally separated from the reaction mass and reused in the carbonylation. If necessary, of course, makeup material may be added to this stream.

The methyl isobutyrate and methanol may be separated by any conventional means. In one particular technique, azeotropic distillation is used wherein a liquid paraffin, preferably having a boiling point of 30° C. to 150° C., is added to form a low boiling azeotrope with the methanol. The ambient pressure boiling point of the octane/methanol azeotrope is approximately 65° C., while the methyl isobutyrate has an ambient pressure boiling point of approximately 90° C. The azeotrope is removed overhead and condensed. This condensate is then mixed with water in a separate vessel wherein an aqueous methanol phase and a paraffin phase, essentially free of methanol, are formed. The organic phase is recycled to the azeotropic distillation column. The aqueous methanol phase is then further distilled to recover methanol as an overhead product for recycle to the aforementioned CH$_3$OH/methyl isobutyrate column.

The products of the carbonylation may be dehydrogenated by several known procedures such as described in U.S. Pat. No. 3,721,705 and British Pat. No. 1,141,625 using conventional dehydrogenation catalysts.

To illustrate more fully the instant invention, attention is directed toward the following example:

To a 600 ml. stirred autoclave at 20° C. is added 100 g. of a BF$_3$.CH$_3$OH catalyst. A 9:1 carbon monoxide/propylene mixture is added to the autoclave at 60 atm. The mixture is heated to 50° C. and held at this temperature for one hour. A sample taken from the autoclave is analyzed by gas-liquid chromatography. All of the propylene is converted and the selectivity to methyl isobutyrate is 94%. The autoclave is cooled, depressurized, and then repressurized again to 60 atm. with the 9:1 gas mixture. This procedure is repeated several times until about 50% of the methanol in the catalyst reacts. The mixture remaining in the autoclave is again analyzed and found to be approximately a 2:1:1 mixture of boron trifluoride/methanol/methyl isobutyrate (about 38 wt. % isobutyrate). The selectivity to the methyl isobutyrate is 88%.

The subject invention is illustrated by treating the reaction mass in accordance with the following sequence: The reaction mixture is introduced into a distillation flask wherein the liberated BF$_3$ is removed overhead at a temperature of 60° C. and a pressure of 100 mm Hg. This BF$_3$ is recycled to the autoclave for reuse as hereinafter described.

This leaves in the distillation flask a solution containing a 1:1:1 ratio BF$_3$/methanol/methyl isobutyrate complex. To this, sufficient methanol is added to convert the solution to a 1:10:1 molar ratio. The resulting solution is distilled at a pressure of 10 mm Hg until the overhead temperature reaches 80° C. to separate a methyl isobutyrate/methanol azeotrope. Continued distillation at 80° C. removes additional methanol. Analysis of the materials remaining in the distillation flask shows the presence of a 1:2 BF$_3$/methanol complex. This latter complex is recycled to the carbonylation reactor with the BF$_3$ initially stripped from the distillation flask.

Octane is added to the methyl isobutyrate/methanol solution and a low boiling azeotrope of methanol and octane is distilled overhead. The residue is methyl isobutyrate. It may be dehydrogenated to form methyl methacrylate.

A direct method of recovering the catalyst components has been attempted but not found successful. For example, a molar excess of sodium chloride was added to the admixture of BF$_3$/methanol/methyl isobutyrate 1:1:1 complex in an attempt to form a complex of the BF$_3$ with the sodium chloride and separate the complex. In this procedure, from the mixture thus formed the methyl isobutyrate and methanol were easily separated by distillation. However, the BF$_3$/sodium chloride complex salt, even after heating to 400° C., did not completely break down into its component salts. Analysis of the BF$_3$ thus recovered indicates that only 50% of the initial BF$_3$ present was recovered.

Still another approach to separating the 1:1:1 complex was to use n-heptane to selectively extract the methyl isobutyrate. Only about 10% of the methyl isobutyrate was extracted into the heptane after extraction with one volume of the heptane for two volumes of the complex.

In still another approach, an admixture of BF$_3$/methanol/methyl isobutyrate in a molar ratio of 1:1:0.5 was introduced to the top of a countercurrent stripping column while nitrogen was passed through the bottom of the column under atmospheric pressure at a temperature of 80° C. The effort to preferentially strip the BF$_3$ was unsuccessful. Analysis showed that no BF$_3$ was removed by this technique. Methyl propionate is produced from ethylene and BF$_3$.CH$_3$OH.

Having thus described my invention, what I claim and desire to protect by Letters Patent is:

1. A process for the carbonylation of an olefin selected from the group consisting of ethylene and propylene which comprises reacting the olefin with carbon monoxide in the presence of a catalyst complex containing equimolar amounts of BF$_3$ and alcohol at a temperature of from 0° C. to 100° C., carrying out said reaction with an internal molar ratio of carbon monoxide to olefin of at least 5:1 until about 50% of the alcohol in said catalyst is consumed, thereby forming a carboxylic acid ester and liberating free BF$_3$; separating sufficient BF$_3$ from the reaction mass by stripping to leave a first residue containing equimolar amounts of the BF$_3$, the alcohol and the carboxylic acid ester; admixing the first residue with additional alcohol; thereafter distilling said admixture to separate overhead an azeotrope of said alcohol and said carboxylic acid ester and additional uncomplexed alcohol until a second residue containing BF$_3$ to alcohol in a molar ratio of 1:2 remains; and thereafter combining said second residue with additional BF$_3$ to form the catalyst complex.

2. The process of claim 1 wherein the additional BF$_3$ added to the second residue is that BF$_3$ initially removed from the reaction mass.

3. The process of claim 1 wherein the olefin is propylene, the catalyst is BF$_3$.CH$_3$OH, and the product obtained is methyl isobutyrate.

4. The process of claim 1 wherein the olefin is ethylene, the catalyst is BF$_3$.CH$_3$OH, and the product obtained is methyl propionate.

5. The process of claim 1 wherein the carboxylic acid ester and alcohol stream is combined with an azeotroping solvent and said combination is subjected to further distillation wherein a low boiling azeotrope comprised of solvent and alcohol is removed from the carboxylic acid ester.

6. The process of claim 5 wherein the azeotroping solvent is a paraffin having a boiling point of from 30° C. to 150° C.

7. The process of claim 6 wherein the paraffin is octane.

* * * * *